(12) United States Patent
Bacchiocchi

(10) Patent No.: US 9,855,118 B2
(45) Date of Patent: Jan. 2, 2018

(54) MODULAR APPARATUS FOR INSTALLATION OF MULTIPLE DENTAL PROSTHESES

(71) Applicant: Danilo Bacchiocchi, Castelfidardo (IT)

(72) Inventor: Danilo Bacchiocchi, Castelfidardo (IT)

(*) Notice: Subject to any disclaimer, the term of this patent is extended or adjusted under 35 U.S.C. 154(b) by 0 days.

(21) Appl. No.: 15/324,115

(22) PCT Filed: Nov. 3, 2014

(86) PCT No.: PCT/EP2014/073582
§ 371 (c)(1),
(2) Date: Jan. 5, 2017

(87) PCT Pub. No.: WO2016/012058
PCT Pub. Date: Jan. 28, 2016

(65) Prior Publication Data
US 2017/0202646 A1    Jul. 20, 2017

(30) Foreign Application Priority Data

Jul. 23, 2014  (IT) .............................. AN2014A0111

(51) Int. Cl.
*A61C 8/00* (2006.01)

(52) U.S. Cl.
CPC .......... *A61C 8/0027* (2013.01); *A61C 8/0048* (2013.01)

(58) Field of Classification Search
CPC ....... A61C 8/0027; A61C 8/0048; A61C 8/00; A61C 8/0028; A61C 8/0053
See application file for complete search history.

(56) References Cited

U.S. PATENT DOCUMENTS

| 5,219,286 A * | 6/1993 | Hader ................. | A61C 8/0048 433/172 |
| 2003/0108845 A1* | 6/2003 | Giovannone ........ | A61C 8/0048 433/173 |
| 2004/0018469 A1 | 1/2004 | Summers | |
| 2004/0078040 A1* | 4/2004 | Feijtel ................. | A61C 13/275 433/173 |
| 2004/0142300 A1* | 7/2004 | Aravena .............. | A61C 8/0048 433/76 |
| 2007/0281283 A1* | 12/2007 | Lundgren ............. | G09B 23/32 433/214 |
| 2008/0171307 A1* | 7/2008 | Wilcox ................ | A61C 8/0048 433/222.1 |
| 2010/0209874 A1* | 8/2010 | Auderset ............. | A61C 13/275 433/174 |
| 2011/0195379 A1* | 8/2011 | Allaire ................. | A61C 8/0048 433/174 |

(Continued)

FOREIGN PATENT DOCUMENTS

| DE | 19748268 A1 | 5/1999 |
| EP | 0393324 A1 | 10/1990 |

OTHER PUBLICATIONS

International Search Report for corresponding International Application No. PCT/EP2014/073582.

*Primary Examiner* — Nicholas Lucchesi
(74) *Attorney, Agent, or Firm* — Egbert Law Offices, PLLC

(57) ABSTRACT

A modular apparatus for installation of multiple dental prostheses being adapted to connect and join various cylindrical stumps protruding from the maxillary or mandibular bone of a patient.

4 Claims, 6 Drawing Sheets

(56) References Cited

U.S. PATENT DOCUMENTS

2012/0214128 A1* 8/2012 Collins ............... A61C 8/0012
433/173
2013/0171586 A1* 7/2013 Anitua Aldecoa ... A61C 8/0027
433/173

* cited by examiner

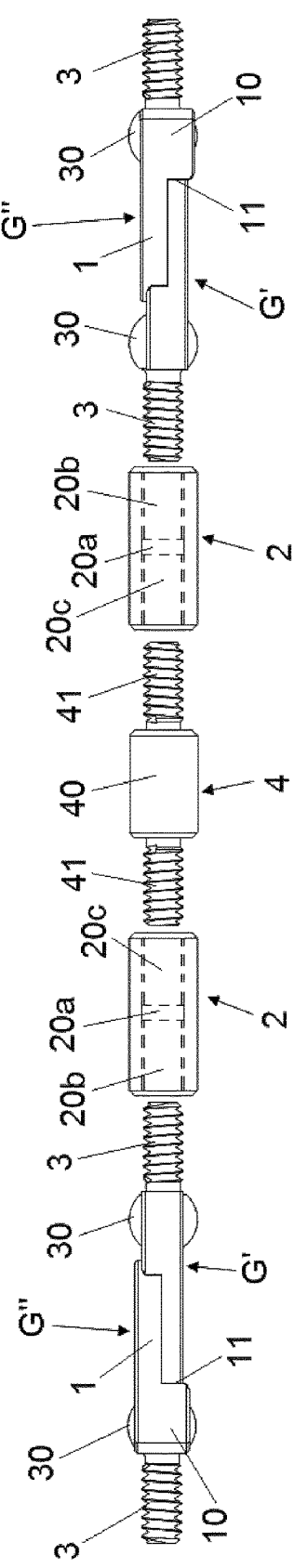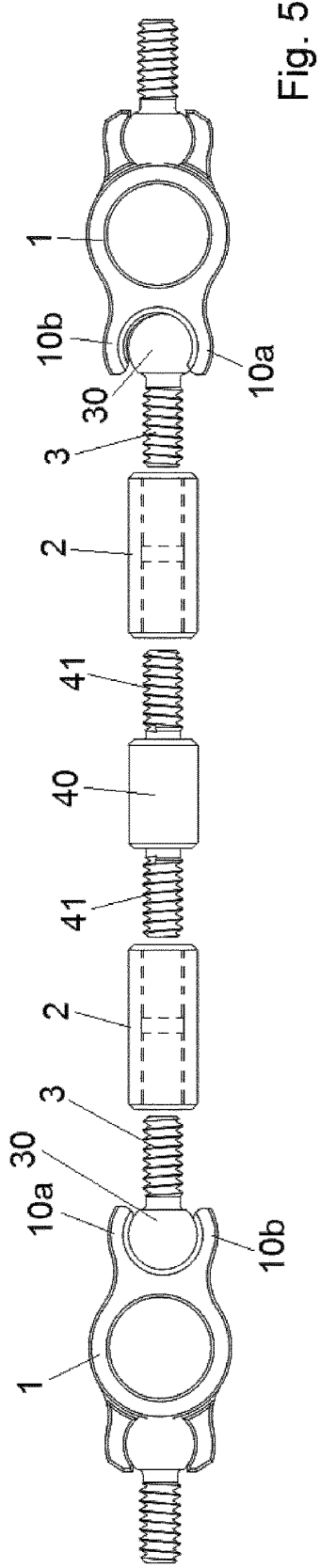

MODULAR APPARATUS FOR INSTALLATION OF MULTIPLE DENTAL PROSTHESES

The present patent application for industrial invention relates to a modular apparatus for installation of multiple dental prostheses.

The peculiarities and advantages of the invention will become evident after a short description of the prior art.

Firstly, it must be noted that dental prostheses basically consist in artificial teeth used to replace "natural" teeth that have been extracted or have fallen out.

Similar prostheses may be individual prostheses, when they consist in a single artificial tooth, or multiple prostheses, when they consist in a plurality of artificial teeth disposed in adjacent position. Multiple prostheses can be used to replace the entire upper or lower dental arch of the patient.

In particular, an individual dental prosthesis is normally formed of three cooperating elements.

The first element consists in a basically cylindrical metal pin (technically defined as "implant"), which is adapted to be screwed into the maxillary or mandibular bone of the patient.

The second element consists in a cylindrical metal stem (technically defined as "stump"), which is adapted to be screwed into a corresponding implant in such manner to protrude shortly with respect to the maxillary or mandibular bone.

The third element consists in a capsule made of resin or ceramic, which is the artificial tooth and is permanently fixed to the stump.

On the contrary, during the installation of multiple prostheses, two or more specimens of the implant must be implanted into the maxillary or mandibular bone and corresponding specimens of the stump must be installed on each implant.

Then, the various stumps that protrude from the bone must be joined with a connection element, which can cover either a curved or a rectilinear trajectory, following either completely or partially the natural anatomic curve of the section of the maxillary or mandibular bone where the multiple dental prosthesis is to be installed.

As a matter of fact, such a metal structure has a bearing and connection function with respect to the bone for an acrylic or composite resin cast that, after incorporating it completely, reproducing the gingival profile, is provided with the capsules that act as artificial teeth.

An especially critical aspect of this technology is the connection of the various stumps that protrude from the bone.

Up to now, according to the intra-oral welding technique with immediate load implantology, a similar need is satisfied by mounting a titanium bar on the back of the various stumps, towards the inside of the is oral cavity, said titanium bar being permanently fixed with a welding point applied in correspondence of each stump.

Moreover, it must be considered that the connection element must be positioned in a suitable point of the height of the various stumps, in order to guarantee the good outcome of the resin cast used to incorporate the entire metal structure.

However, it is impossible to fix the titanium bar on all consecutive stumps, while always centering it vertically and horizontally with respect to the bone crests because welding is lateral with respect to each stump.

A similar impossibility depends on the fact that the various stumps to be connected do not have a perfect vertical position.

As a matter of fact, it is common for one or more of said stumps to have a sub-vertical position because the implants are screwed into the maxillary or mandibular bone with higher or lower inclination, also for anatomical reasons.

Because of the different inclination of the stumps, and because of the need to weld such connection bar always in centered position with respect to the stumps, it is necessary to model the bar before welding it to the stumps.

In particular, the bar has a basically "broken" profile, in which sections with substantially horizontal direction (when the two stumps connected by the bar are perfectly parallel) alternate with sections with sub-horizontal direction (when the two stumps connected by the bar have a different inclination with respect to the vertical axis).

It is evident that, for each multiple prosthesis to be installed, the misalignment conditions of the stumps may be very different with respect to the conditions of the preceding and the following prostheses. In view of the above the operator in charge of installing the various prostheses must model the bar used to connect the various stumps in a "dedicated", not repetitive way.

The operator must make an artesanal work that, on one side, is requires a high ability and, on the other side, inevitably increases the installation time of the entire multiple prostheses.

Additionally, it must be considered that the connection bar is welded in a lateral point of each stump, in a condition that favors the generation of stress and/or unbalanced extension between the two cooperating elements, thus impairing the stability of the entire dental prosthesis.

The specific purpose of the present invention is to facilitate and accelerate the installation of the connection element between the various stumps of a multiple dental prosthesis during the installation.

More precisely, the purpose of the present invention is to avoid the artesanal approach (reference is made to the "dedicated" modeling of the traditional metal bar) in connecting the various stumps of the prosthesis, and provide a solution that, while still adjusting to the specific needs with high precision, uses an extremely linear, precise and reliable mounting principle, which is generally based on the execution of a few simple repetitive operations.

Similar purposes are achieved with the modular apparatus of the invention, which allows for connecting the various stumps of a multiple prosthesis by means of a sort of chain formed of an articulated series of substantially horizontal rods, in which each rod interposed between two consecutive stumps can have a different length and inclination with respect to each other rod of the same chain.

Obviously, the different length and the different inclination of each rod of the chain provided with the apparatus of the invention allow for making up the vertical misalignment between the two stumps to be connected by a corresponding rod.

In such a perspective, the apparatus of the invention is composed of two main elements, which are regularly alternated between the various stumps to be connected.

The first element consists in a substantially cylindrical rod, is provided with an extensible structure formed of multiple coaxial elements that are helically coupled; said rod being provided with a ball at each end.

The second element consists in a joint adapted to be mounted in each stump in order to act as connection means between the stump and the two specimens of the rod among which the latter is interposed.

The joint consists in a ring adapted to be exactly inserted into a stump, as well as externally provided with a radial fork having a basically semi-circular profile, adapted to exactly receive one of the balls mounted at the ends of the rod, allowing for free rotation and providing an articulated "spherical joint" coupling.

When the stump is to be connected to two rods (one on the left and one on the right), it is necessary to insert an overlapped pair of joints on the stump, so that the stump can rely on the presence of one of said radial forks on the left and of another one on the right.

When the stump is to be connected to one rod only, it is necessary to insert only one specimen of the joint on the stump, after directing the fork in a useful position in order to receive the ball of the rod.

As mentioned earlier, the two elements of the apparatus of the invention are adapted to cooperate in order to make up the misalignment between two adjacent stumps.

Practically speaking, such a making up is obtained by allowing the operator in charge of installing the dental prosthesis to change the length and the inclination of each rod interposed between the stumps.

Of course, the discretionary variation of the length of each rod can be obtained by suitably adjusting the mutual position of the aforementioned elements that are coupled helically.

The discretionary variation of the inclination of each rod, with respect to the stumps between which it is interposed, uses two different adjustments of the mutual position of the various elements that form the bearing structure of the dental prosthesis.

Firstly, the variation of the inclination of each rod is executed by is taking advantage of the spherical joint couplings that are established between the spherical ends of the rod and the two forks, which belong to corresponding joints, protruding on the two sides of the same central stump.

In view of the above, the possibility given to each rod to have any inclined position, at the discretion of the installer, makes it possible to have an advantageous connection of the joints provided in two adjacent stumps, also when the joints are situated at different heights because of the different inclination of the stumps with respect to the vertical axis.

In fact, the variation of the inclination of each rod is also affected by the different fixing height given by the installer to each of said joints in the corresponding stump, as well as by the angular deviation given from time to time to the fork of each joint with respect to the axis of the corresponding stump.

After the installer has adjusted the length and the inclination of the rods (as well as the height of each joint), it will be simply necessary to stabilize the position given to all these cooperating elements.

This operation will be carried out by simply applying a series of welding points, the first ones being adapted to stabilize the position of each joint in correspondence of the height given to it inside the stump, whereas the second ones will be used not only to permanently join each ball of the rods to the fork of the joint cooperating with it, but also, and most of all, to prevent the additional free rotation of the balls that would evidently cause the uncontrolled unwanted variation of the inclination angle of the rod.

In particular, it must be considered that the welding points used to stabilize the coupling between each ball and the corresponding fork are made on two diametrally opposite positions with respect to the ball, basically at the height of each of the two branches of the fork.

Also the fixing of each joint with the corresponding stump is guaranteed by means of two welding points made on two diametrally is opposite positions.

The symmetrical conditions guarantee the perfectly balanced fixing between all the aforementioned elements, such to prevent the generation of any stress and/or deformation between them.

For explanatory reasons, the description of the invention continues with reference to the attached drawings, which only have an illustrative, not limiting value, wherein:

FIGS. 4 and 5 are respectively an exploded side view and an exploded top view of some elements of the apparatus according to the present invention;

Figure 1:
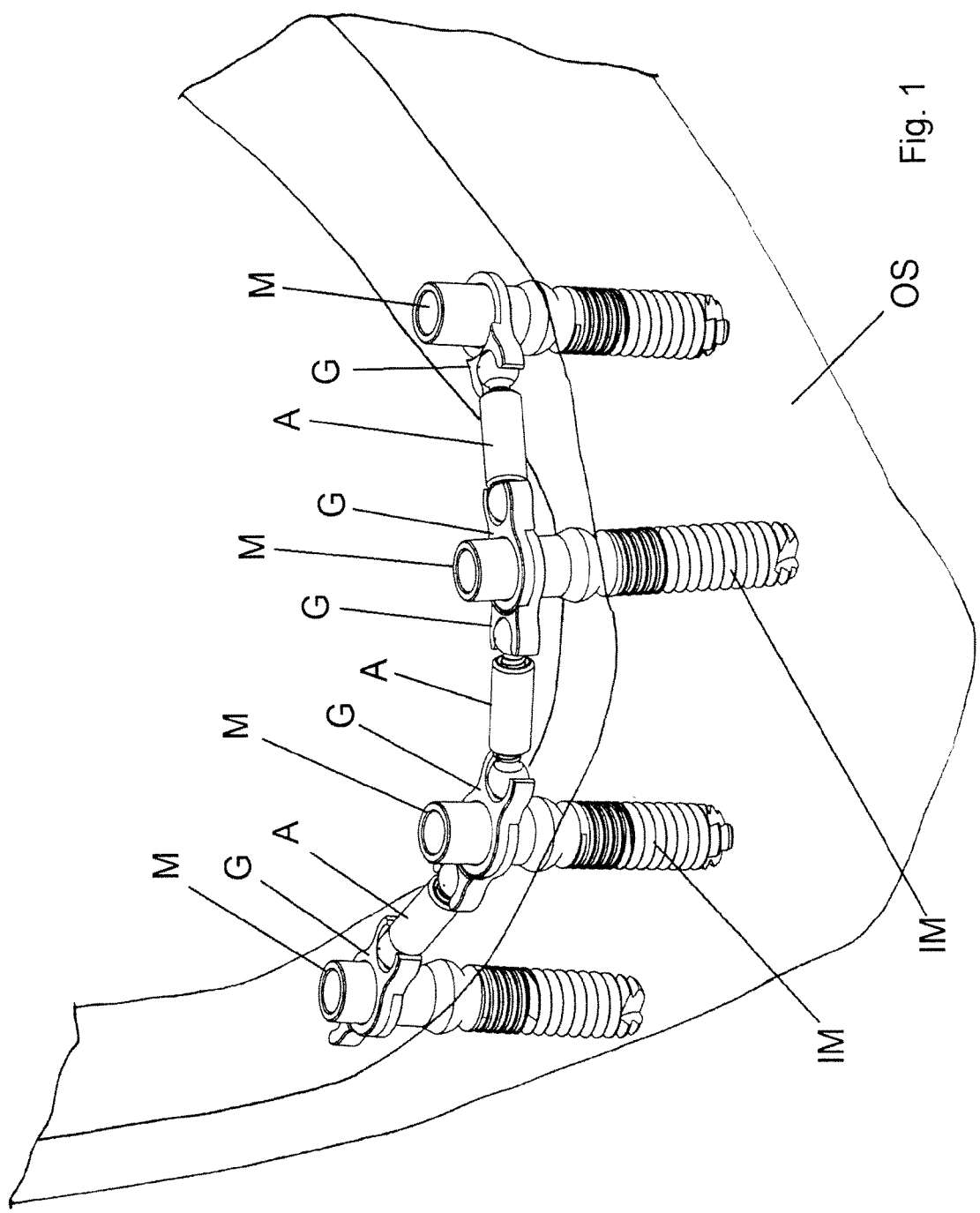
FIG. 1 is a diagrammatic view that shows the bearing structure of a multiple prosthesis obtained with the modular apparatus of the invention.

With reference to FIG. 1, the modular apparatus of the invention is used to connect and join the stumps (M) of a typical multiple dental prosthesis that normally protrude from implants (IM) screwed into the mandibular or maxillary bone (OS) of the patient.

As mentioned above, the apparatus of the invention is composed of two main cooperating elements, or modules, which are adapted to be used, from time to time, in a number of specimens that corresponds to the number of stumps (M) to be connected; it being also provided that both elements have a completely metal structure.

Figure 2:
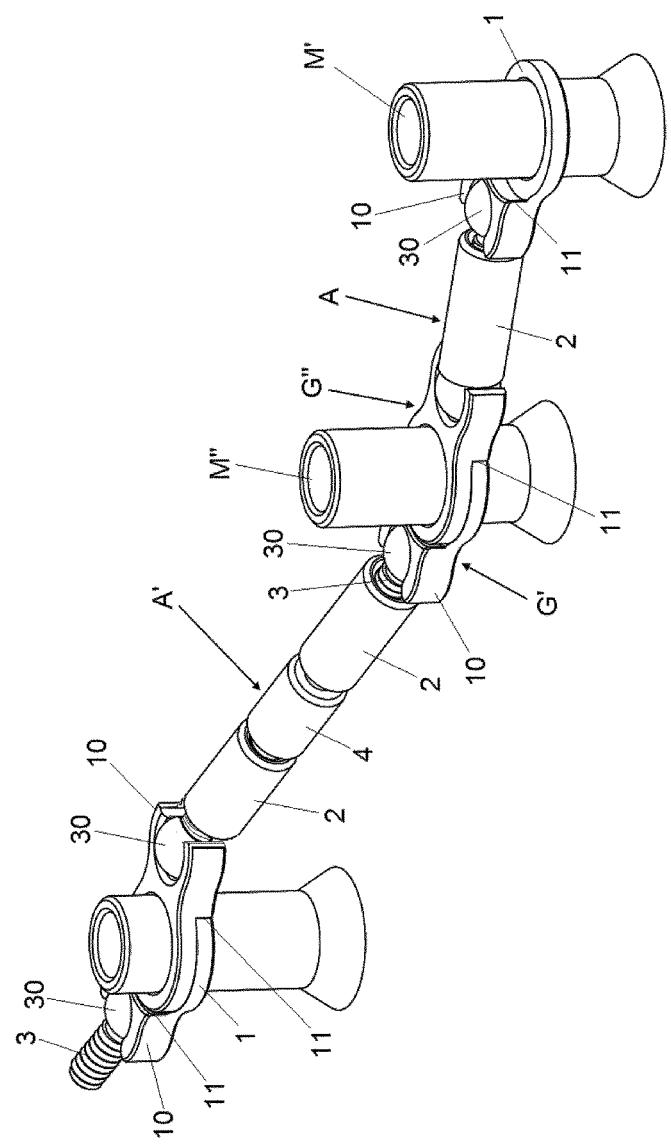
FIG. 2 is an axonometric view of a possible solution according to which the apparatus of the invention is used to connect three stumps of a multiple dental prosthesis.

The first element, or module, of the apparatus of the invention is a a joint (G) basically consisting in a ring (1) adapted to be slidingly and revolvingly inserted outside a typical stump (M) of a dental prosthesis, as expressly shown in FIG. 2.

Figure 7C:
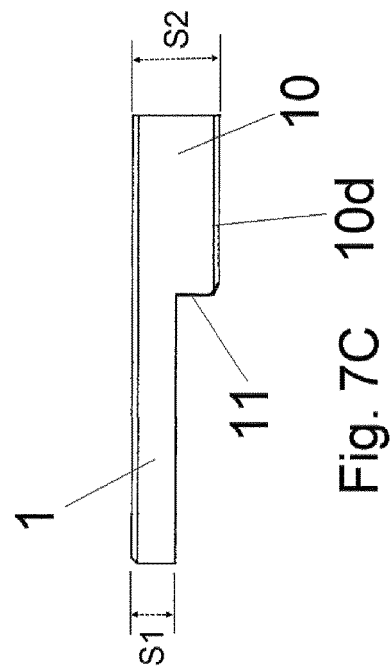
FIGS. 7A, 7B and 7C are respectively an axonometric view, a top view and a side view of an additional element of the apparatus according to the present invention, expressly adapted to cooperate with the element shown in FIG. 6.
Figure 7A:
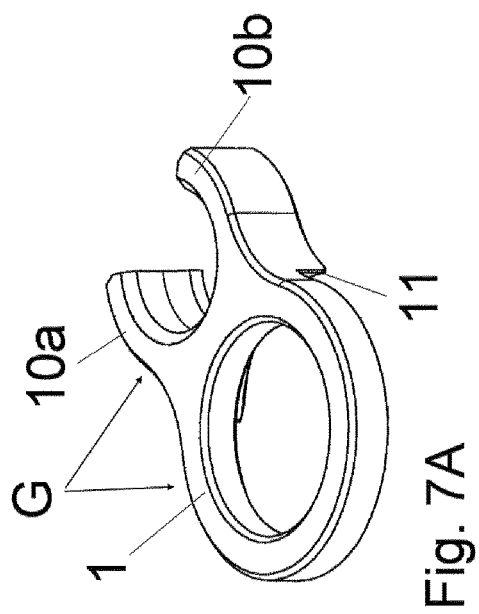
Figure 7B:
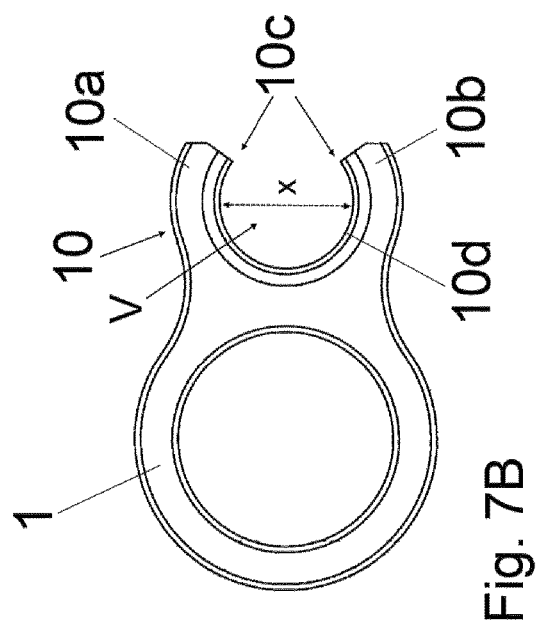

Moreover, as shown in FIGS. 7A, 7B and 7C, the ring (1) is provided, in a section of its external circumference, with a radial fork (10) formed of two rounded branches (10a, 10b) in symmetrically opposite position, defining an intermediate compartment (V) that perimetrally extends for an arc higher than a semi-circumference; it being provided that the opening (10c) of the fork (10) has a width lower than the maximum distance (x) internally measured in the fork (10) between the two branches (10a, 10b).

A tapered edge (10d) is provided at the base of the compartment (V) in order to reduce the section of the compartment (V) in such point.

As shown in FIG. 8C, the thickness (S1) of the two branches (10a, 10b) of the fork (10) is substantially double than the thickness (S2) of the bearing ring (1), so that a vertical shoulder (11) with rounded profile is generated between the radial fork (10) and the ring (1).

The second element, or module, of the apparatus according to the present invention consists in an extensible rod (A) that is formed of some cooperating elements that, being mutually connected by means of helical coupling, provide the entire rod (A) with a variable length that can be selectively chosen according to the specific user needs.

As mentioned above, the specific function of the rod (A) is to connect and join two consecutive stumps (M) of a multiple prosthesis, taking advantage of the cooperation of two specimens of joint (G) that is are suitably installed on the stumps (M).

With reference to FIGS. 4 and 5, each rod (A) is composed of a short tube with circular section (2) that is internally provided, at approximately half of its length, with a vertical partition (20a) adapted to separate two identical cylindrical ducts (20b, 20c) provided with internal threaded walls.

Figure 6:
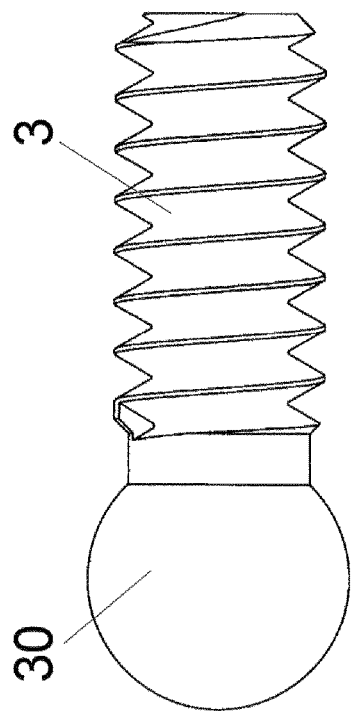
FIG. 6 is a side view of an element of the apparatus according to the present invention.

The other elements that are used to complete the rod (A) consist in two specimens of a threaded stem (3) ending with a ball (30) at one side, as expressly shown in FIG. 6.

The diameter of each threaded stem (3) corresponds to the section of the ducts (20b, 20c) of the short tube (2), whereas each ball (30) is configured like an enlarged head with respect to the stem (3).

In fact, the two threaded stems (3) are adapted to penetrate progressively, by means of helical coupling, inside the threaded cylindrical ducts (20b, 20c) of the short tube (2) in such manner that the balls (30) protrude from the two ends of the short tube (2).

Moreover, it must be noted that each ball (30) is adapted to be exactly inserted, with freedom of rotation in all directions, inside the compartment (V) of the fork (10) of a joint (G), obtaining a typical "spherical joint" coupling, in which the threaded bearing stem (3) of each ball (30) basically occupies the opening (10d) of the fork (10).

It must be noted that the tapered edge (10d) provided at the base of each fork (10) is used to prevent the ball (30) from coming out of the fork (10) because of simple gravity.

In the foreground FIG. 2 shows a first embodiment of the rod in its short version (A), which is formed of one specimen of the short tube (2) and of two specimens of the threaded stem (3) and is expressly adapted to be used to connect two stumps (M, M') disposed at a close distance.

FIG. 2 also shows the cooperation between the rod (A), the two stumps (M, M') between which the same is position and the two specimens of joint (G) inserted on the stumps (M, M').

Firstly, a specimen of the joint (G) is inserted into each of said is stumps (M, M'), then the two balls (30) provided at the ends of the rod (A) are inserted from up down into the forks (10) belonging to the two joints (G).

Evidently, if the stump is the last one of the series, as in the case of the stump (M') shown at the far right end of FIG. 2, a single specimen of the joint (G) is to be inserted into it.

If, on the contrary, the stump occupies an intermediate position between two other stumps, as in the case of the stump (M") shown in the center of FIG. 2, two specimens of the joint (G) are to be inserted into it.

In such a situation, the two specimens of the joint (G) are adapted to be exactly interfaced one onto the other, mutually penetrating and originating a prismatic coupling that reduces the vertical volume.

More precisely, the first of the joints (G') is inserted into the stump (M') in such a position that the shoulder (11) is faced upwards, whereas the second joint (G") is inserted in the stump (M) in overturned position, i.e. with the shoulder (11) faced downwards.

Therefore, after bringing into mutual contact the rings (1) of the two joints (G', G"), the shoulder (11) of the joint (G") in upper position is stopped against the external border of the ring (1) of the joint (G') in lower position, whereas the shoulder (11) of the joint (G') in lower position is stopped against the external border of the ring (1) of the joint (G") in upper position.

The additional consequence of the above is that the two interfaced joints (G) form a perfectly compact body, without undercut either in lower or upper position, because the total thickness of the two overlapped rings (1) is equal to the thickness of the corresponding forks (10).

Figure 3:
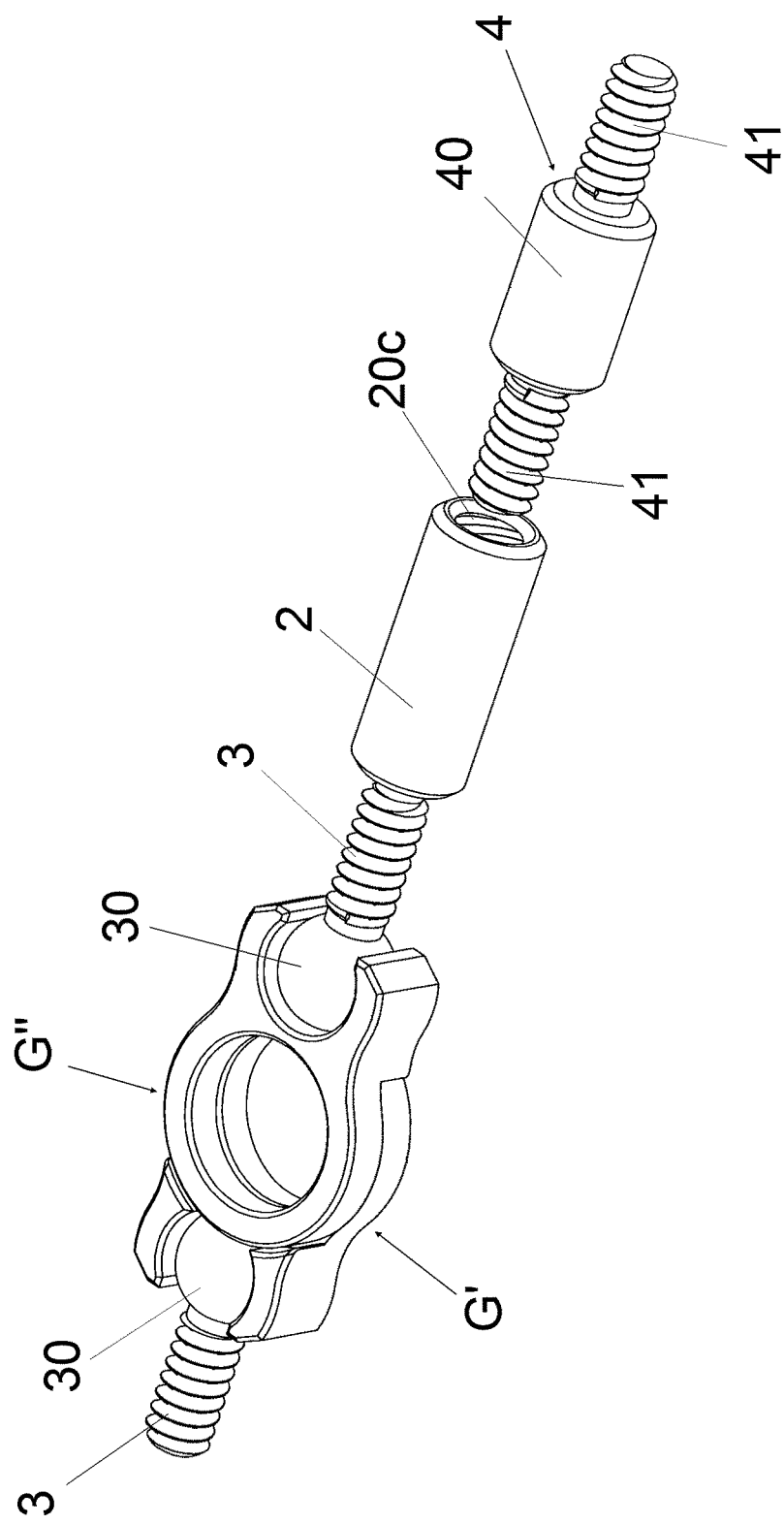
FIG. 3 is an exploded axonometric view of the cooperation of some elements of the apparatus according to the present invention.

FIG. 2—in combination with FIGS. 3 and 4—shows the configuration of the rod in its long version (A'), which is adapted to be installed between two stumps positioned at a considerable distance.

A similar long version of the rod (A') is composed of the following five cooperating elements:
two specimens of the short tube (2)
two specimens of the threaded stem (3) with ball (30)
one specimen of a pin (4) adapted to helically connect the two specimens of the short tube (2).

In particular, the pin (4) is formed of a central cylindrical body (40) substantially having the same diameter as the short tube (2) and of two identical threaded pins (41) that axially diverge from opposite sides from the central body (40) and are adapted to be exactly inserted and helically coupled with said cylindrical ducts (20b, 20c) provided in each specimen of the short tube (2).

The installation of the long version of the rod (A') provides for screwing the two threaded pins (41) of the pin (4), specifically one into the first cylindrical duct (20b) of the short tube (2) positioned on the right-hand side and one into the second cylindrical duct (20c) of the cylindrical ducts of the short tube (2) positioned on the left-hand side.

Now it is simply necessary to provide for the helical coupling of the two specimens of the threaded stem (3) in correspondence of the two cylindrical ducts (20b, 20c) that are still free of the two specimens of the short tube (2), in such manner to generate, also at the two ends of the long version of the rod (A'), the pair of balls (30) adapted to cooperate, as illustrated above, with a corresponding pair of joints (2) inserted in correspondence of the two stumps (M) between which the rod (A') is installed. also at the two ends of the long version of the rod (A').

Such a detailed description provides a better understanding of the logic principle that allows for adjusting the elements (G, A) of the apparatus of the invention.

As mentioned above, the installer of a multiple prosthesis can choose the position of each joint (G) with respect to the stump (M), by making the ring (1) provided in the joint (G) slide vertically along the stump (M).

Moreover, the installer can choose the correct angular position of the fork (10) that belongs to the same joint (G), by using the free rotation of the ring (1) of the joint with respect to the stump (M).

After correctly choosing the height of each joint (G) and the angular position of the fork (10), the installer can stabilize the position of the joint (G) with a welding line applied between the joint (G) and the surface of the stump (M).

An additional operation is the adjustment of the length and inclination of the various rods (A) adapted to be disposed between the corresponding pairs of stumps (M), it being evident that such a double adjusting is necessary to adjust each rod to the specific distance between the two stumps (M), to the difference in height between the two joints (G) inserted on the stumps (M), and to the vertical misalignment of the stumps (M).

The length of the short version of the rod (A) can be adjusted by adjusting the depth of the helical coupling of the two specimens of the threaded stem (3) provided with ball (30) inside the two ducts (20b, 20c) of a short tube (2) in intermediate position between them.

On the other hand, the length of the long version of the rod (A') can be adjusted by adjusting the depth of the coupling of the threaded pins (41) of the connection pin (4) in the two ducts (20b, 20c) of the two specimens of the short tube (2) between which the pin is positioned.

In such a case, an additional adjustment of the length of the long version of the rod (A') is also related with the higher or lower depth given to the helical coupling between the two specimens of the threaded stem (3) with ball (30) in the cylindrical ducts (20c, 20b) that are free and belong to the two specimens of the short tube (2).

Finally, the inclination of each rod (A) between two adjacent stumps (M) can be easily adjusted by means of the spherical joint coupling established between each ball (30) provided at the ends of the rod (A) and the fork (10) of the joint (G) inserted into the stump (M).

Also in this case, after giving the correct inclination to each rod (A), the installer of the prosthesis will stabilize such a position by applying a welding point between the ball (30) and each of the branches (10a, 10b) of the fork (10) of the joint (G).

Suitable welding points must be also applied in correspondence of all helical couplings in each rod (A), after defining the correct position of the apparatus of the invention inside the patient's mouth.

Figure 9A:
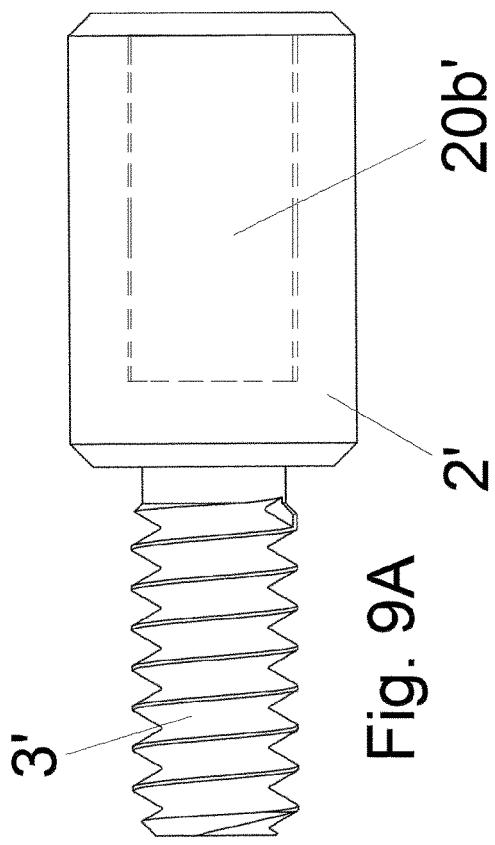
FIGS. 9A and 9B are a side view and an axonometric view of an alternative embodiment of another element of the apparatus according to the present invention.
Figure 9B:
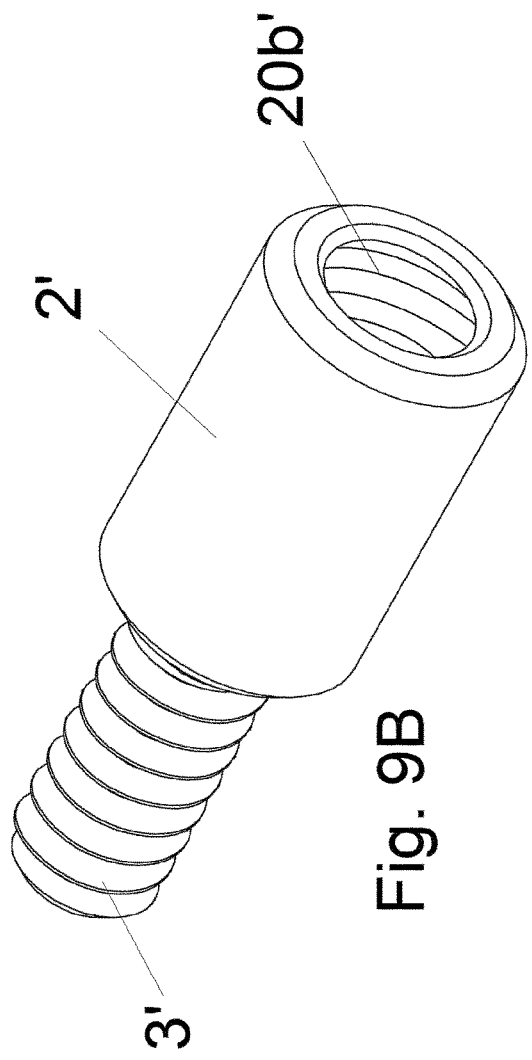
Figure 8:
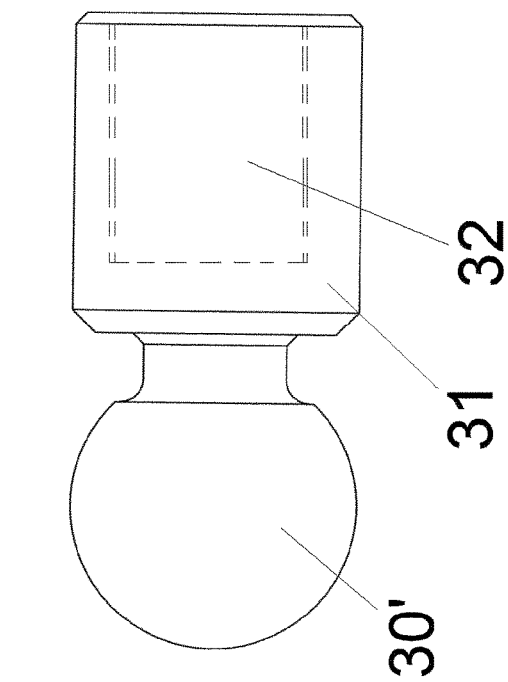
FIG. 8 is an alternative embodiment of the element shown in FIG. 6.

With reference to FIGS. 8, 9A and 9B, it must be noted that, while still falling within the scope of the present invention, the rod (A) can have a different embodiment, which is completely equivalent from the functional viewpoint to the one described with reference to the preceding figures.

While still providing for the helical coupling of the various elements of each rod (A) in order to allow for the easy adjustment of the total length of the rod (A), a different configuration can be given to the two ending balls (30) and the adjacent short tube (2).

As shown in FIG. 8, in such a case, the ball (30') is associated with a nozzle (31) that is internally provided with a cylindrical duct (32) with threaded walls (32).

As shown in FIGS. 9A and 9B, the short tube (2') is provided on one side with one of the cylindrical ducts (20c) with threaded internal walls and on the other side with a threaded stem (3') adapted to be helically coupled with said cylindrical duct (32) provided in the nozzle (31) associated with the ball (30).

A similar coupling between the short tube (2') and the nozzle (31) of a ball (30') allows for assembling the structure of a rod (A) only at one end.

Evidently, a second ball (30') must be mounted at the opposite end of the rod (A) in order to complete the structure of the rod (A).

In order to do that, after coupling another specimen of the ball (30') provided with nozzle (31) with another specimen of the short tube (20') provided with threaded stem (3'), the operator must simply install a specimen of the pin (4) shown in FIGS. 3, 4 and 5 between the two short tubes (20').

The invention claimed is:

1. A modular apparatus for installation of multiple dental prostheses formed of a plurality of implants inserted in a maxillary or mandibular bone and of a corresponding member of cylindrical stumps that protrude from the bone, the modular apparatus comprising:
    a joint having a ring adapted to be slidably and revolvingly inserted outside the stump and an external circumference with a radial fork formed of two rounded branches and symmetrically opposite positions, said joint defining an intermediate compartment that extends perimetrally in an arch greater than a semi-circumference and ends at a base with a tapered edge adapted to reduce a section of the rounded branches, wherein said radial fork has an opening, the opening of said radial fork having a width less than a maximum distance between the two rounded branches; and
    a rod having a cylindrical element adapted to be helically coupled in correspondence with each end by a threaded stem, said rod coupled with a ball adapted to be exactly inserted and freely rotatable into said intermediate compartment of said radial fork of said joint, said cylindrical element comprising a short tube with a circular section, said short tube having a vertical partition therein at approximately half of a length of said short tube, said vertical partition separating two identical cylindrical ducts each having internal threaded walls, said threaded stem being cooperative with said ball, said threaded stem being helically coupled inside one of said two identical cylindrical ducts.

2. The modular apparatus of claim 1, wherein the radial fork of said joint has a thickness that is substantially double a thickness of said ring so as to define a vertical shoulder with a rounded profile between said radial fork and said ring.

3. The modular apparatus of claim 1, said cylindrical element comprising two short tubes, said threaded stem comprising two threaded stems provided with said ball, each of said two threaded stems adapted to be coupled with one of the two identical cylindrical ducts, a pin formed of a central cylindrical body with a substantially similar diameter an a diameter of the short tube, said cylindrical body having two ends, said pin comprising threaded axial pins disposed at said two ends of said cylindrical body, the axial threaded pin having a diameter identical to a diameter of said threaded stem, wherein each of the threaded axial pins is adapted to be helically coupled with one of said two identical cylindrical ducts of one of said two short tubes when said pin is disposed in an intermediate position between the two short tubes.

4. A modular apparatus for installation of multiple dental prostheses formed of a plurality of implants inserted in a maxillary or mandibular bone and of a corresponding member of cylindrical stumps that protrude from the bone, the modular apparatus comprising:
    a joint having a ring adapted to be slidably and revolvingly inserted outside the stump and an external circumference with a radial fork formed of two rounded branches and symmetrically opposite positions, said joint defining an intermediate compartment that extends perimetrally in an arch greater than a semi-circumference and ends at a base with a tapered edge adapted to reduce a section of the rounded branches, wherein said radial fork has an opening, the opening of said radial fork having a width less than a maximum distance between the two rounded branches; and
    a rod having a cylindrical element adapted to be helically coupled in correspondence with each end by a threaded stem, said rod coupled with a ball adapted to be exactly inserted and freely rotatable into said intermediate compartment of said radial fork of said joint, wherein said cylindrical element comprises two short tubes each with a circular section, said two short tubes each having a cylindrical duct with threaded walls at one end thereof and for approximate one half of a length thereof, each of said two short tubes having said threaded stem at an opposite ends thereof, said threaded stem adapted to be helically coupled with a threaded cylindrical duct inside a nozzle of respective balls, and a pin having a central cylindrical body with a substantially identical diameter as a diameter of the short tube, said central cylindrical body having a threaded axial pin at each end thereof, the threaded axial pin having a diameter identical to a diameter of the threaded stem, the threaded axial pin adapted to be helically coupled with the cylindrical ducts of the short tube, said pin disposed between the two short tubes.

* * * * *